United States Patent
Lapham

(10) Patent No.: US 9,393,180 B2
(45) Date of Patent: Jul. 19, 2016

(54) MEDICATION ALARM, DISPENSER AND RECORDS ARCHIVE SYSTEM AND APPARATUS

(71) Applicant: Shannon Lee Lapham, Nathrop, CO (US)

(72) Inventor: Shannon Lee Lapham, Nathrop, CO (US)

(*) Notice: Subject to any disclaimer, the term of this patent is extended or adjusted under 35 U.S.C. 154(b) by 2 days.

(21) Appl. No.: 14/540,407

(22) Filed: Nov. 13, 2014

(65) Prior Publication Data

US 2016/0136056 A1 May 19, 2016

(51) Int. Cl.
| | |
|---|---|
| *G08B 1/00* | (2006.01) |
| *A61J 7/04* | (2006.01) |
| *G06F 19/00* | (2011.01) |
| *A61J 7/00* | (2006.01) |
| *B65D 83/04* | (2006.01) |

(52) U.S. Cl.
CPC ............. *A61J 7/0481* (2013.01); *A61J 7/0076* (2013.01); *B65D 83/04* (2013.01); *G06F 19/3462* (2013.01); *B65D 2585/56* (2013.01)

(58) Field of Classification Search
CPC ...... A61J 7/0481; A61J 7/0076; B65D 83/04; B65D 2585/56; G06F 19/3462
USPC ......... 340/309.16, 573.1; 368/10, 244; 221/3, 221/8
See application file for complete search history.

(56) References Cited

U.S. PATENT DOCUMENTS

| | | | |
|---|---|---|---|
| 4,682,299 A | 7/1987 | McIntosh | |
| 5,020,037 A | 5/1991 | Raven | |
| 5,347,453 A | 9/1994 | Maestre | |
| 5,915,558 A | 6/1999 | Girvetz | |
| 6,004,020 A | 12/1999 | Bartur | |
| 6,390,327 B1 | 5/2002 | Cornell | |
| 7,044,302 B2 | 5/2006 | Conley | |
| 7,877,268 B2 | 1/2011 | Kulkarni | |
| 2002/0149472 A1* | 10/2002 | Roe ...................... | A61J 7/0481 340/309.16 |
| 2006/0139150 A1* | 6/2006 | Brue ..................... | A61J 7/0481 340/309.16 |
| 2012/0006708 A1* | 1/2012 | Mazur .................. | A61J 7/0481 206/438 |
| 2013/0195326 A1* | 8/2013 | Bear ..................... | A61J 7/0076 382/128 |
| 2014/0064038 A1 | 3/2014 | Duer | |
| 2014/0166529 A1* | 6/2014 | Fung ..................... | A61J 7/04 206/534 |

* cited by examiner

*Primary Examiner* — Anh V La
(74) *Attorney, Agent, or Firm* — The Keys Law Firm PLLC

(57) ABSTRACT

A medication alarm, dispenser and records archive system and apparatus for providing interactive alert and informational functions in conjunction with a partitioned medication receptacle. Such an interactive medication receptacle system comprises an interactive electronic section slidably disposed on a pill storage section. The storage section includes a plurality of discrete compartments, each labeled with a day of the week. The electronic section includes an electronic touch screen with its front surface, a USB receptacle on its top side, and a processing housing that extends internally across the entire width of the top of electronic section and includes the primary operative computer components of the interactive medication receptacle system. The entire internal area of the electronic section below the processing housing is substantially hollow, thereby enabling it to slide over and encase the storage section.

6 Claims, 2 Drawing Sheets

MEDICATION ALARM, DISPENSER AND RECORDS ARCHIVE SYSTEM AND APPARATUS

BACKGROUND OF THE INVENTION

1. Field of the Invention

This invention relates generally to medication dispensing systems and, more particularly, to a system and apparatus having a medication alarm, storage, and records archive.

2. Description of the Prior Art

The use and design of partitioned medication receptacles that separate pills to be taken based on a day and/or time into discrete compartments disposed on a single housing is well known. Indeed, such receptacles are typically defined by a plurality of discrete compartments, each with separate access lids, all disposed in a single housing. One of such housings may include one or two compartments for each day of the week and enough total compartments to allow medication for an entire week or month to be stored therein and retrieved therefrom. Advantageously, an individual's medications for an extended period of time can be stored in a partitioned receptacle that allows medications solely for a particular desired moment can be retrieved without disturbing the other stored medications.

A problem which still exists, however, is that despite such organization and storage capability, conventional partitioned medication receptacles often lack the ability to be configured to provide interactive services appurtenant to the medication protocol of the user. Thus, there remains a need for a medication alarm, dispenser and records archive system and apparatus which could be programmed to provide a sensory alert to the user when it was time to take the medication. It would be helpful if such an interactive medication receptacle system was electronically configured at the time a medication was prescribed (or at the time the prescription was fulfilled) to provide such sensory alerts. It would be additionally desirable for such an interactive medication receptacle system to provide a visual user interface that could provide display not only alerts but additional information about the patient, including medical history.

The Applicant's invention described herein provides for a medication alarm, dispenser and records archive system and apparatus adapted to alert a user when it was time to take the medication in one of its discrete compartments. The primary components of Applicant's interactive medication receptacle system are a pill storage section, an interactive electronic section, and communications interface member. When in operation, the interactive medication receptacle system enables all pertinent information pertaining to a user's prescribed medication treatments to be provided to the user at relevant times. As a result, many of the limitations imposed by prior art structures are removed.

SUMMARY OF THE INVENTION

A medication alarm, dispenser and records archive system and apparatus for providing interactive alert and informational functions in conjunction with a partitioned medication receptacle. Such a interactive medication receptacle system comprises an interactive electronic section slidably disposed on a pill storage section. The storage section includes a plurality of discrete compartments, each labeled with a day of the week. The electronic section includes an electronic touch screen with its front surface, a USB receptacle on its top side, and a processing housing that extends internally across the entire width of the top of electronic section and includes the primary operative computer components of the interactive medication receptacle system. The entire internal area of the electronic section below the processing housing is substantially hollow, thereby enabling it to slide over and encase the storage section.

It is an object of this invention to provide a medication alarm, dispenser and records archive system and apparatus which could be programmed to provide a sensory alert to the user when it was time to take the medication.

It is another object of this invention to provide an interactive medication receptacle system which was electronically configured at the time a medication was prescribed (or at the time the prescription was fulfilled) to provide such sensory alerts.

It is yet another object of this invention to provide an interactive medication receptacle system to provide a visual user interface that could provide display not only alerts but additional information about the patient, including medical history.

These and other objects will be apparent to one of skill in the art.

DETAILED DESCRIPTION OF THE INVENTION

Figure 1:
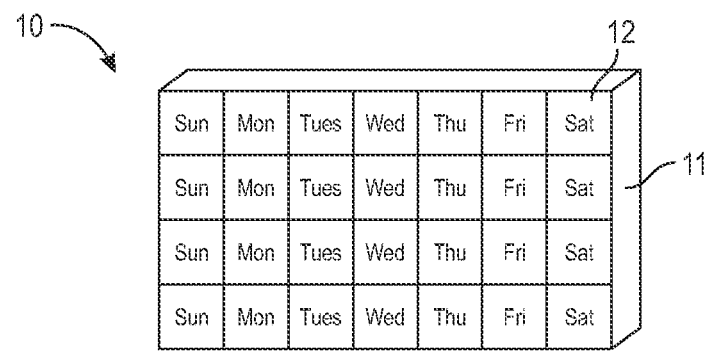
FIG. 1 is a front perspective view of an exemplary embodiment of a conventional, prior art partitioned medication receptacle.

Referring now to the drawings and in particular FIG. 1, a conventional partitioned medication receptacle 10 is shown having a housing 11 that includes a plurality of discrete compartments 12, each labeled with a day of the week. In such conventional designs, it is understood that each partition 12 has its own separate top that opens independent of the tops of the other partitions, thereby allowing a single compartment to be accessed without disturbing the other partitions.

Figure 2:
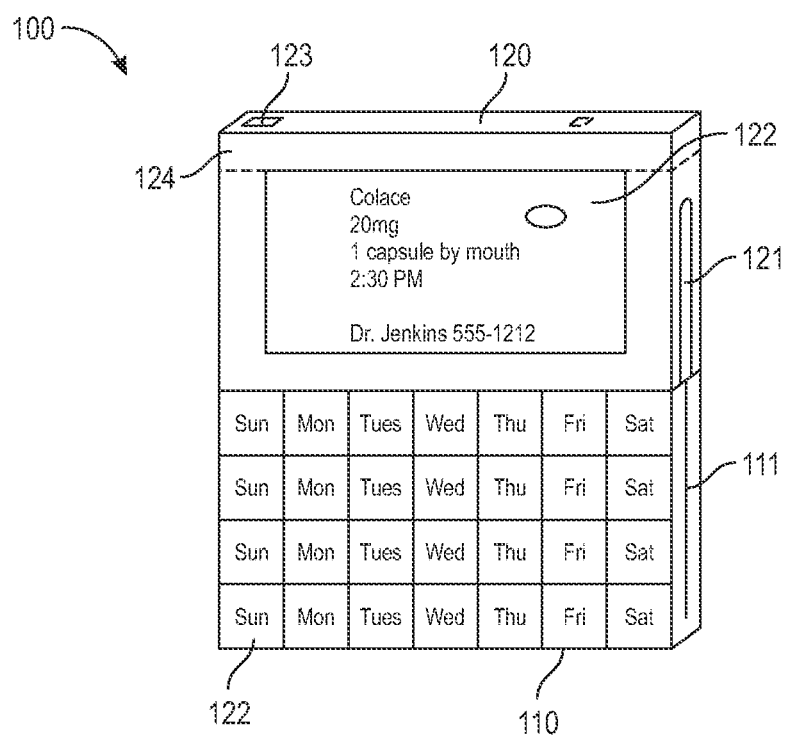
FIG. 2 is a front perspective view of an interactive medication receptacle system built in accordance with the present invention in its open position.
Figure 3A:
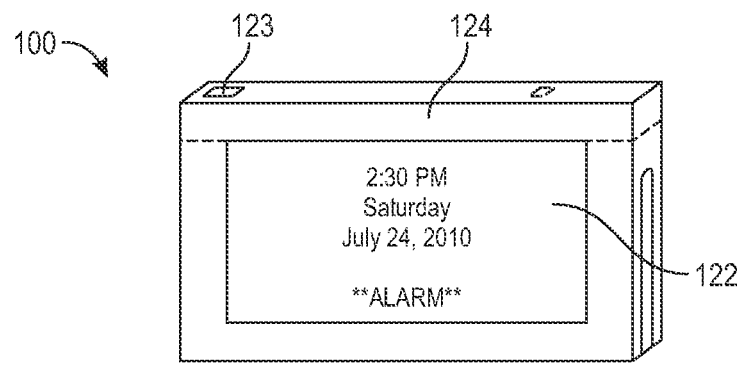
FIG. 3A is a front perspective view of an interactive medication receptacle system built in accordance with the present invention in its closed position showing an alert condition.
Figure 3B:
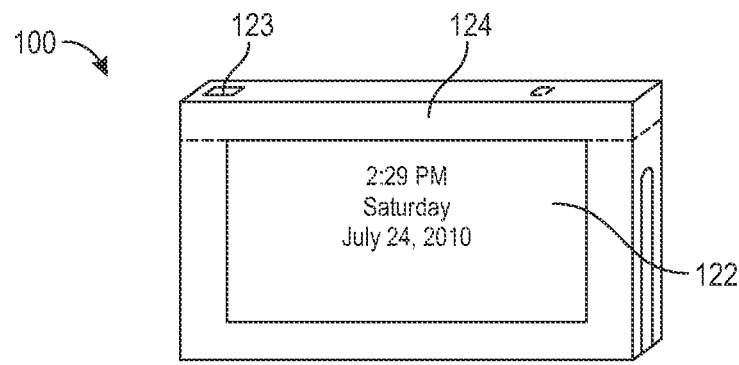
FIG. 3B is a front perspective view of an interactive medication receptacle system built in accordance with the present invention in its closed position.

Referring now to FIGS. 2, 3A, and 3B, an interactive medication receptacle system 100 built in accordance with the present invention is shown having a pill storage section 110 and an interactive electronic section 120. In the preferred embodiment, the interactive electronic section 120 is slidably disposed on the storage section 110, having a slot 121 integral with its side wall that engages a track 111 that extends from each side of the storage section 110. In this regard, the electronic section 120 can slide between an open position, as illustrated by FIG. 2, and a closed position, as illustrated by FIGS. 3A and 3B.

Similar to conventional partitioned medical receptacles, the storage section 110 includes a plurality of discrete compartments 112, each labeled with a day of the week. The electronic section 120 includes a display interface 122 integral with its front surface, a communications interface member 123 on its top side, and a processing housing 124 that extends internally across the entire width of the top of electronic section 120. The entire internal area of the electronic section below the processing housing 124 is substantially hollow, thereby enabling it to slide over and encase the storage section 110 as shown in FIGS. 3A and 3B.

In the preferred embodiment, the display interface 122 defines an electronic touch screen which provides a visual output of alert information, medication information, and medical history information that is stored electronically on the interactive medication receptacle system 100 as well as a user input interface for receiving commands and other manual inputs from a user.

The communications interface member 123, defined in the preferred embodiment as a USB receptacle, receives a USB plug to allow data such as alert information, medication information, and medical history information to be electronically input into the interactive medication receptacle system 100 as well as to allow the input of electricity for powering the interactive medication receptacle system 100.

Inside the processing housing 124 are the primary operative computer components of the an interactive medication receptacle system 100, including a processor, non-volatile memory, a battery, a vibrator and a speaker. Such operative computer components facilitate the operation of the display interface 122 communications interface member 123 as well as the tracking of time for alerting purposes, the generation of audible and tactile alerts, and the storage of electronic data and the formatting for its display.

In the preferred embodiment, the interactive medication receptacle system 100 measures seven inches by seven inches when in its closed position.

It is contemplated that the display interface 122 may be utilized to provide distinct access permissions and outputs to various users of the interactive medication receptacle system 100, such as patient users, doctor/pharmacist users, and emergency medical practitioner users. As such, it is understood that while a patient user may simple be alerted of when to take medication, provided information on the medication being taken on the screen (see FIG. 2), and allowed to clear an alert, a doctor/pharmacist user and/or emergency medical practitioner user may be able to review medical history information on the patient and input information through the same. Similarly, while the communications interface member 123 may be used by a patient user simply to recharge the battery of the device, it may be used by a doctor/pharmacist user and/or emergency medical practitioner user to load prescription plans, alert schedules, and medical history information.

In use, it is contemplated that the interactive medication receptacle system would be programmed electronically or manually by a doctor (or assistant) when medications are prescribed, or by a pharmacist when prescriptions are fulfilled. A patient user would then keep the interactive medication receptacle system with them and receive sensory alerts at the times set during programming, reminding them to take their medication and availing information on the medication to be taken. In addition, for a doctor, pharmacist, or emergency medical person, the interactive medication receptacle system provides a system that allows on site research of a patient's history prior to performing or prescribing any treatment.

Figure 4:
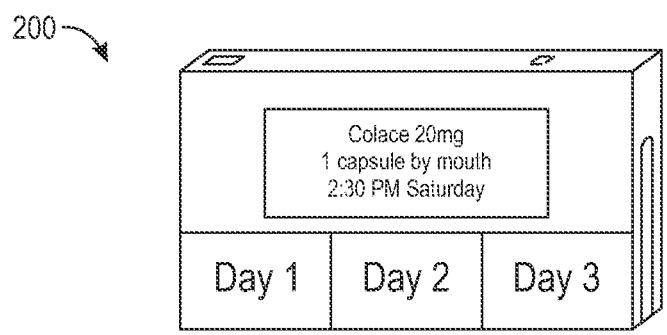
FIG. 4 is a front perspective view of an interactive medication receptacle system built in accordance with an alternate embodiment the present invention in its open position.

Referring now to FIG. 4, a miniature version of an interactive medication receptacle system 200 is shown. It is contemplated that this version of the interactive medication receptacle system 200 would operate as the standard version disclosed in FIGS. 2, 3A, and 3B, but would be sized smaller because it would include fewer medication compartments.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An interactive medication receptacle system, comprising:
   a pill storage section body having a front storage side, a left storage side and a right storage side, wherein said front storage side includes a plurality of discrete compartments and at least one of said left storage side and said right storage side include a track;
   an interactive electronic section body having a front electronic side, a left electronic side, a right electronic side, and a processing housing, wherein said front electronic side includes a display interface and an input interface, at least one of said left electronics side and said right electronics side include a slot that corresponds to the track on the at least one of said left storage side and said right storage side, and said processing housing includes a processor, memory, a power supply, and at least one a vibrator and speaker, each electrically interconnected with each other and to the display interface and input interface;
   said processor adapted to provide access to a plurality of classifications of users and modulate a display interface output based on an identified classification of user at a given moment; and
   said interactive electronic section body configured to slidably engage said pill storage section body, thereby allowing the interactive electronic section body to move between an open position in which the plurality of discrete compartments are exposed to a closed position wherein the plurality of discrete compartments are enclosed by the interactive electronic section body.

2. The interactive medication receptacle system of claim 1, wherein said interactive electronic section body additionally includes a communications interface member that enables electricity to be supplied to the power supply and data to be communicated with the memory.

3. The interactive medication receptacle system of claim 2, wherein said communications interface member defines a USB receptacle.

4. The interactive medication receptacle system of claim 1, wherein:
   said left storage side and said right storage side include a track; and
   said left storage side and said right storage side each include a slot that corresponds to the tracks on said left storage side and said right storage side.

5. The interactive medication receptacle system of claim 1, wherein said processing housing includes the vibrator and speaker.

6. The interactive medication receptacle system of claim 1, wherein said display interface and input interface define an electronic touch screen.

* * * * *